United States Patent

Sutcu et al.

[11] Patent Number: 5,921,984
[45] Date of Patent: Jul. 13, 1999

[54] BIPOLAR ELECTROSURGICAL INSTRUMENT WITH COAGULATION FEATURE

[75] Inventors: Maz Sutcu, New Hartford; John Gentelia, Madison, both of N.Y.

[73] Assignee: Conmed Corporation, Utica, N.Y.

[21] Appl. No.: 08/904,615

[22] Filed: Aug. 1, 1997

Related U.S. Application Data

[63] Continuation of application No. 08/352,042, Nov. 30, 1994, abandoned.

[51] Int. Cl.$^6$ .................................................. A61B 17/39
[52] U.S. Cl. .............................. 606/46; 606/48; 606/50; 606/51
[58] Field of Search .................... 606/48, 50, 51, 606/46, 174

[56] References Cited

U.S. PATENT DOCUMENTS 5,356,408  10/1994  Rydell ........................................ 606/48
5,403,312  4/1995  Yates et al. .
5,496,317  3/1996  Goble et al. .............................. 606/48

FOREIGN PATENT DOCUMENTS 0624348  11/1994  European Pat. Off. .................. 606/51

*Primary Examiner*—Lee Cohen

[57] ABSTRACT

A bipolar electrosurgical instrument for cutting and coagulating tissue is disclosed. Also disclosed is a method for using the bipolar electrosurgical instrument. The instrument includes particular patterns of electrically conductive portions and electrically non-conductive portions on the interior surfaces of the shearing members such that the electrical current is localized in the tissue to be treated without causing a short circuit in the instrument. Other advantages of the device include an improved cutting ability aided by the localized electrical current and reduced manufacturing costs as compared to similar, prior art devices.

2 Claims, 4 Drawing Sheets

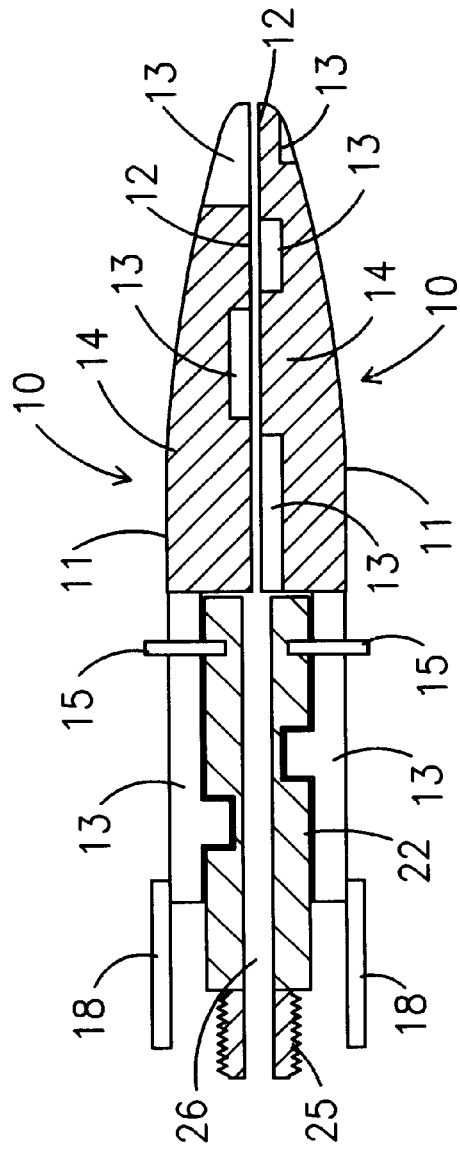
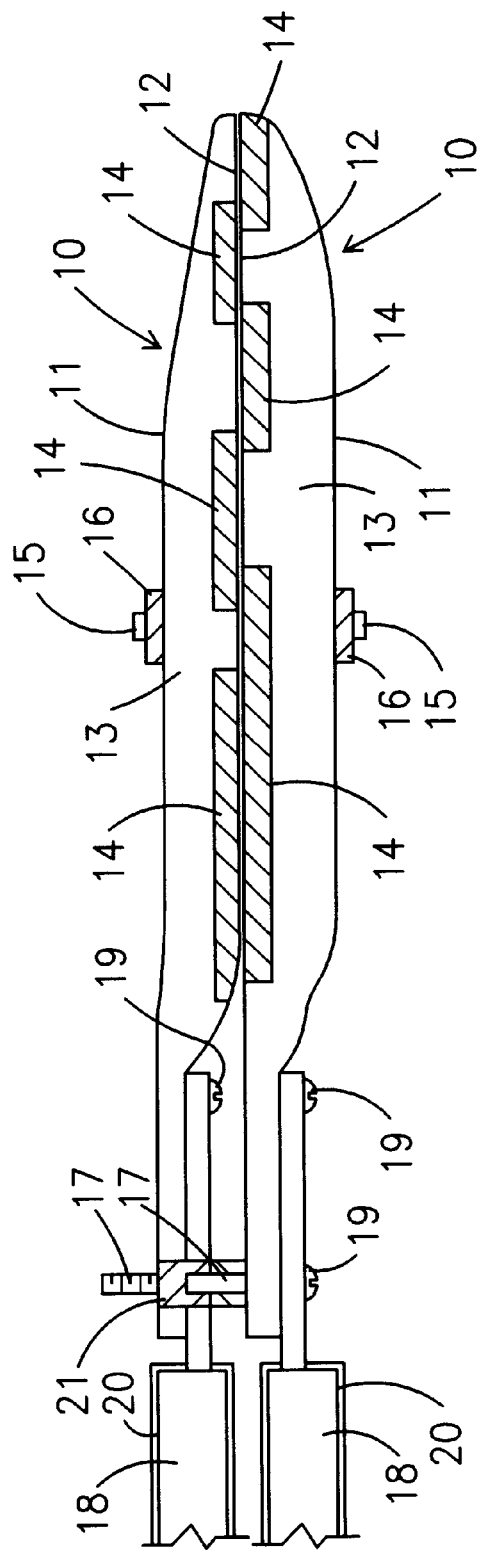

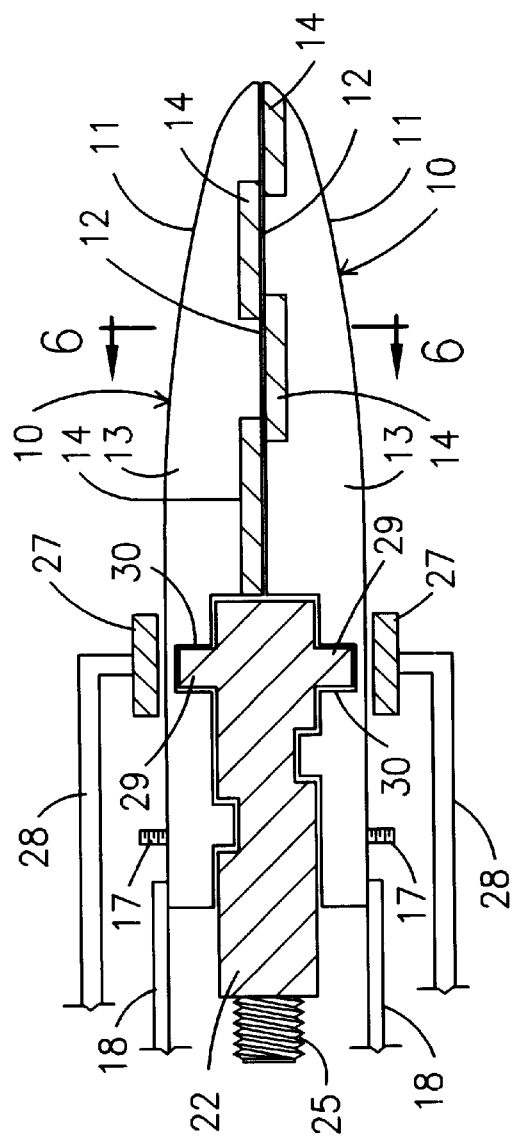
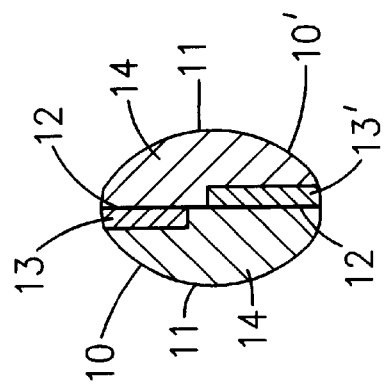
Fig. 5
Fig. 6

BIPOLAR ELECTROSURGICAL INSTRUMENT WITH COAGULATION FEATURE

This application is a continuation of application Ser. No. 08/352,042 filed Nov. 30, 1994, now abandoned.

FIELD OF THE INVENTION

The invention relates generally to the design of a bipolar electrosurgical instrument. More particularly, the invention relates to electrosurgical scissors incorporating bipolar electrodes such that mechanical cutting and electrocoagulation are accomplished simultaneously in an improved manner.

BACKGROUND OF THE INVENTION

The control of bleeding during surgery is an important issue. Electrosurgical techniques that pass a current through the patient's tissue between two electrodes for both cutting and causing hemostasis to tissue are known. The current passing through the tissue causes heating of the tissue as a function of the current density and the resistance of the tissue. Such heating causes the tissue proteins to form coagulum that seals the bleeding sites.

In bipolar electrosurgical devices, two electrodes are closely spaced together to thereby confine current flow locally to the tissue disposed between the electrodes. One difficulty encountered with prior art electrosurgical devices is that of controlling the current flow to the patient's tissue such that no undesirable trauma is brought about in adjacent tissue. Although bipolar electrosurgical devices have helped to localize current flow, these devices have yet to be optimized in this respect. Further, some of these devices present difficulties in selectively applying the current flow.

For example, U.S. Pat. No. 3,651,811 describes bipolar electrosurgical scissors having opposing cutting blades forming active electrodes. This device enables a surgeon to sequentially coagulate the blood vessels contained in the tissue and mechanically sever the tissue with the scissor blades. However, since the blades form the electrodes, coagulation must be a separate step from cutting in order to avoid contact between two scissor blades so that they do not short circuit.

One proposed solution to this problem can be found in U.S. Pat. Nos. 5,352,222 and 5,356,408. These patents disclose bipolar electrosurgical scissors wherein each cutting blade includes a cutting surface, an electrically non-conductive layer and an electrically conductive outer surface which serves as the electrode.

However, these devices suffer from three important disadvantages. First, they require a three layer laminate which makes them difficult to manufacture. Second, the flow of electric current through the tissue is not sufficiently localized by these devices since the current must flow from the back of one cutting blade element to the back of the other cutting blade element. Finally, since the current is not applied directly via the cutting surface, this device does not optimize cutting and coagulation.

Another bipolar electrosurgical cutting apparatus is disclosed in U.S. Pat. No. 5,324,289. In one embodiment disclosed in this patent, one of the cutting surfaces is made of a conductive material and serves as an electrode while the other cutting surface is covered by a coating of a non-conductive material. Thus, in this device, the current flows from the surface of one cutting edge to the back side of the other cutting edge. Accordingly, this device suffers from the same disadvantage as the previous device in that the flow of electric current is not sufficiently localized to prevent trauma to adjacent tissue and provide optimum cutting and coagulation.

Thus, a need exists for improvements in bipolar electrosurgical instruments in order to further localize current flow, reduce manufacturing costs and improve the overall efficiency of such devices.

OBJECTS OF THE INVENTION

It is the primary object of the present invention to provide a bipolar electrosurgical instrument which localizes the flow of current to a greater extent than prior art devices.

It is a further object of the present invention to provide a bipolar electrosurgical instrument which is easy to manufacture.

It is a still further object of the present invention to provide a bipolar electrosurgical instrument which localizes the point of highest current density in the tissue of the patient at the point where it is most needed to accomplish coagulation.

It is a still further object of the present invention to provide a bipolar electrosurgical cutting instrument which applies the current to the tissue of the patient in a manner whereby the electrical current aids in the cutting action of the cutting instrument.

These and other objects of the present invention will be apparent from the summary and detailed descriptions which follow.

SUMMARY OF THE INVENTION

In a first embodiment, the present invention relates to a bipolar electrosurgical instrument for cutting and coagulating tissue. The instrument includes first and second shearing members each having an interior surface and an exterior surface. The interior surfaces of the shearing members include an electrically conductive portion and an electrically non-conductive portion, which portions are positioned such that the electrically conductive portions of the interior surfaces do not contact each other through the full range of the scissors-like motion of the shearing members. The instrument also includes a means for pivotally joining said first and second shearing members with their respective interior surfaces facing one another. The instrument also includes a means coupled to at least one of the first and second shearing members for imparting a scissors-like motion relative to the other of said shearing members and a means for applying a voltage between the electrically conductive portions of the interior surfaces of the first and second shearing members.

In a further embodiment of the invention, the bipolar electrosurgical instrument is adapted for attachment to an endoscope, laparoscope or similar apparatus.

In a further embodiment of the present invention, the electrically conductive portion is located on the upper half of interior surface of the first shearing member and the electrically conductive portion of the second shearing member is located on the lower half of the interior surface thereof, allowing for a small space of electrically non-conductive material therebetween in order to prevent contact of the electrically conductive portions during use of the instrument. In this manner the electrical current can be applied across the shearing members through the full range of scissors-like motion without causing a short circuit.

In another embodiment of the present invention, the electrically conductive portions are spaced at intervals on the interior surfaces of the shearing members such that the electrically conductive portion of one shearing member opposes with an electrically non-conductive portion of the other shearing member through the full range of scissors-like motion. In this manner, the current can be applied across the two interior surfaces of the shearing members without causing a short circuit of the device.

Finally, the present invention also relates to a method of using bipolar electrosurgical instruments to simultaneously cause coagulation in tissue while mechanically severing that tissue. The first step in the method is the provision of first and second shearing members each having an interior surface and an exterior surface and wherein the interior surface of the first shearing member includes an electrically conductive portion and the interior surface of the second shearing member includes an electrically conductive portion. The shearing members are connected together so that the interior surfaces move in opposition through a range of motion in a scissors-like action that defines a cutting point moving along the interior surfaces of the shearing members through the range of motion. The second electrically conductive portion is positioned such that it does not contact the first electrically conductive portion through the full range of scissors-like motion of the shearing members.

The method further includes the steps of connecting the electrodes to a power supply, selecting and maintaining a voltage level output across the power supply, placing the interior surfaces of the shearing members in electrical contact with the tissue to be cut so that the current passes through the tissue between the first and second electrodes and moving the first and second shearing members through the full range of scissors-like motion to simultaneously coagulate and mechanically sever the tissue.

BRIEF DESCRIPTION OF THE DRAWINGS

FIG. 1 is a side elevation view of a bipolar electrosurgical scissors instrument having two movable, straight shearing members.

FIG. 4 is a cross-sectional view along line 4–4' of FIG. 3 with the shearing members in the closed position rather than in the open position of FIG. 3.

FIG. 5 is a side elevation view of another embodiment of the bipolar electrosurgical scissors instrument suitable for use in endoscopic or similar procedures.

FIG. 6 is a cross-sectional view along lines 6–6' of FIG. 5 except that it depicts a different design for the electrically conductive portions than is shown in FIG. 5.

DETAILED DESCRIPTION OF THE PREFERRED EMBODIMENTS

Figure 2:
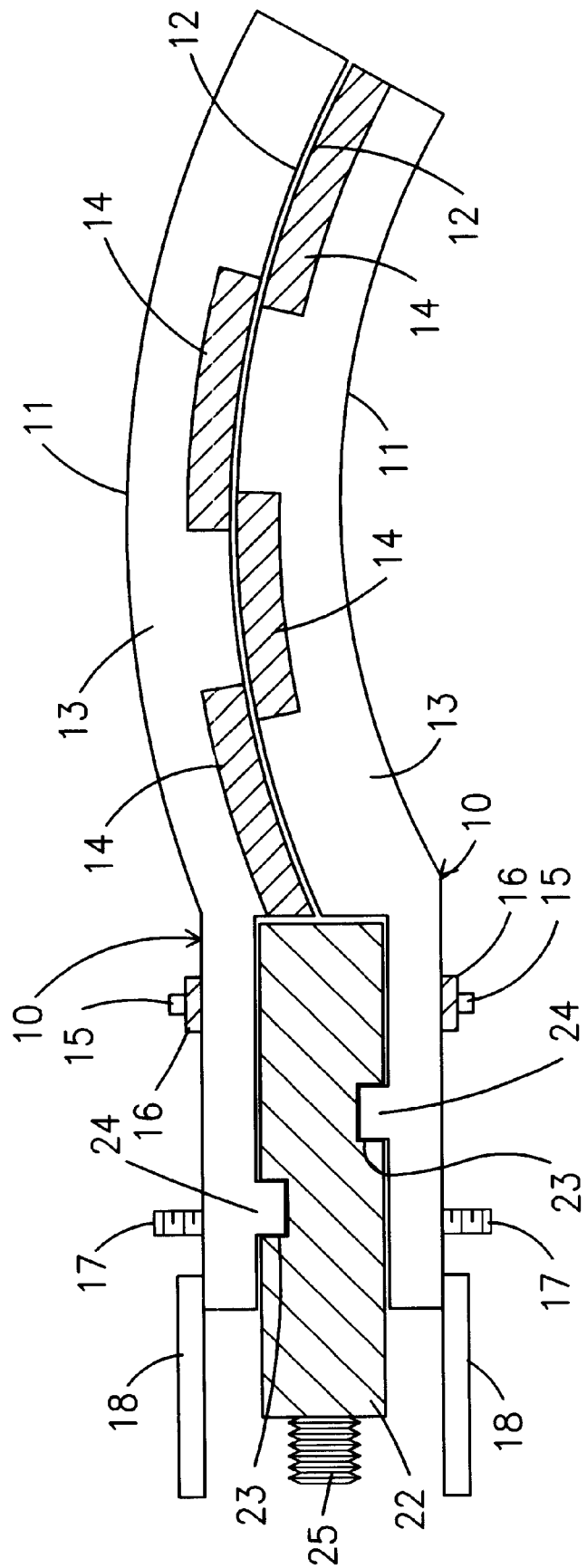
FIG. 2 is a side elevation view of a second embodiment of a bipolar electrosurgical scissors instrument having movable, curved shearing members and suitable for use in endoscopic or similar procedures.

Referring now to the figures, like elements are represented by like numerals throughout several views.

Referring to FIG. 1, there is shown a bipolar surgical scissors instrument comprising shearing members 10 which have exterior surfaces 11 and interior surfaces 12. Each of the shearing members 10 includes a conductive portion 13 and a non-conductive portion 14. Although it appears that each shearing member 10 includes several non-conductive portions 14, in fact, to simplify manufacturing and improve the structural integrity of the shearing member 10, each of the non-conductive portions 14 shown in this figure are part of a single, larger non-conductive portion 14 which is located within conductive portion 13 as will be shown in later figures. Of course, instruments having a plurality of separate non-conductive portions 14 are also within the scope of the present invention although they are less preferred from a manufacturing standpoint. As can be seen from FIG. 1, non-conductive portions 14 are positioned on interior surfaces 12 of shearing members 10 such that when interior surfaces 12 of shearing members 10 contact one another during cutting, the respective conductive portions 13 of shearing members 10 do not contact one another to thereby cause a short circuit.

Shearing members 10 are affixed together by pivot pin 15 such that the shearing members 10 are capable of a scissors-like motion. In this embodiment, pivot pin 15 may be electrically insulated from conducting portions 13 by a non-conductive insulator 16 which surrounds pivot pin 15.

Conductive portions 13 have electrodes 17 attached thereto. Also attached to conductive portions 13 are gripping means 18 which may be attached by any conventional means such as screws 19. It is preferable to cover gripping means 18 with an insulating material 20 to insulate the user of the electrosurgical instrument from the electric current flowing therethrough. The electrosurgical instrument also includes a non-conductive blocking means 21 which prevents the scissors from contacting one another in the vicinity of gripping means 18.

Referring now to FIG. 2, there is shown an alternative embodiment of the present invention employing curved shearing members 10 which also include exterior surfaces 11 and interior surfaces 12. The curved shearing members 10 are comprised of conductive portions 13 and non-conductive portions 14, with the non-conductive portions 14 being positioned such that when shearing members 10 contact one another during cutting, conductive portions 13 of shearing members 10 do not come into contact with one another to thereby prevent a short circuit.

In this embodiment, the curved shearing members 10 are also affixed to one another by pivot pin 15 which is electrically insulated by non-conductive insulator 16 from the conductive portions 13 of shearing members 10. Pivot pin 15 allows shearing members 10 to move relative to one another in a scissors-like motion. Conductive portions 13 also include electrodes 17 in this embodiment.

In FIG. 2, additional mechanical support is provided to shearing members 10 by a support 22 made of non-conductive material which is affixed to shearing members 10 by pivot pin 15. Support 22 further includes curved channels 23 in the top and bottom surfaces thereof. In this embodiment, conductive portions 13 of shearing members 10 include raised portions 24 which are adapted to ride in curved channels 23 to thereby provide additional mechanical support to shearing members 10 during the scissors-like motion thereof. Another view of the curved channels 23 can be seen in FIG. 3.

In an alternative embodiment, support 22 can include only one curved channel 23 on one surface thereof. In this embodiment, the second surface of support 22 is integrally formed with one of the shearing members 10 such that the remaining shearing member 10 moves relative to the shearing member 10 which is integral with support 22.

Support 22 also includes a threaded tube 25 which is adapted for attachment to an endoscope or similar apparatus.

Threaded tube 25 surrounds a lumen 26 (shown in FIG. 4) which continues through the entire length of support 22 such that the bipolar electrosurgical instrument of the present invention can be employed in endoscopic or similar procedures.

In still another alternative embodiment of the present invention, scissors are provided which have a novel mechanical support which makes them extremely durable. The scissors need not be electrosurgical and are characterized by a support 22 affixed to shearing members 10 by a pivot pin 15 which provides a first means of mechanical support to the shearing members 10. The support also has at least one curved channel 23 therein. At least one of the shearing members 10 will include a ridge 22 which is adapted to ride in curved channel 23 to thereby provide a second means of mechanical support to shearing members 10. Finally, support 22 is positioned between shearing members 10 such that a portion of shearing members 10 adjacent pivot pin 15 rides along the first and second surfaces of support 22 to thereby provide yet a third means of mechanical support for the shearing members 10. Thus, in this embodiment, the forward portion of support 22 also functions as a load bearing surface.

Figure 3:
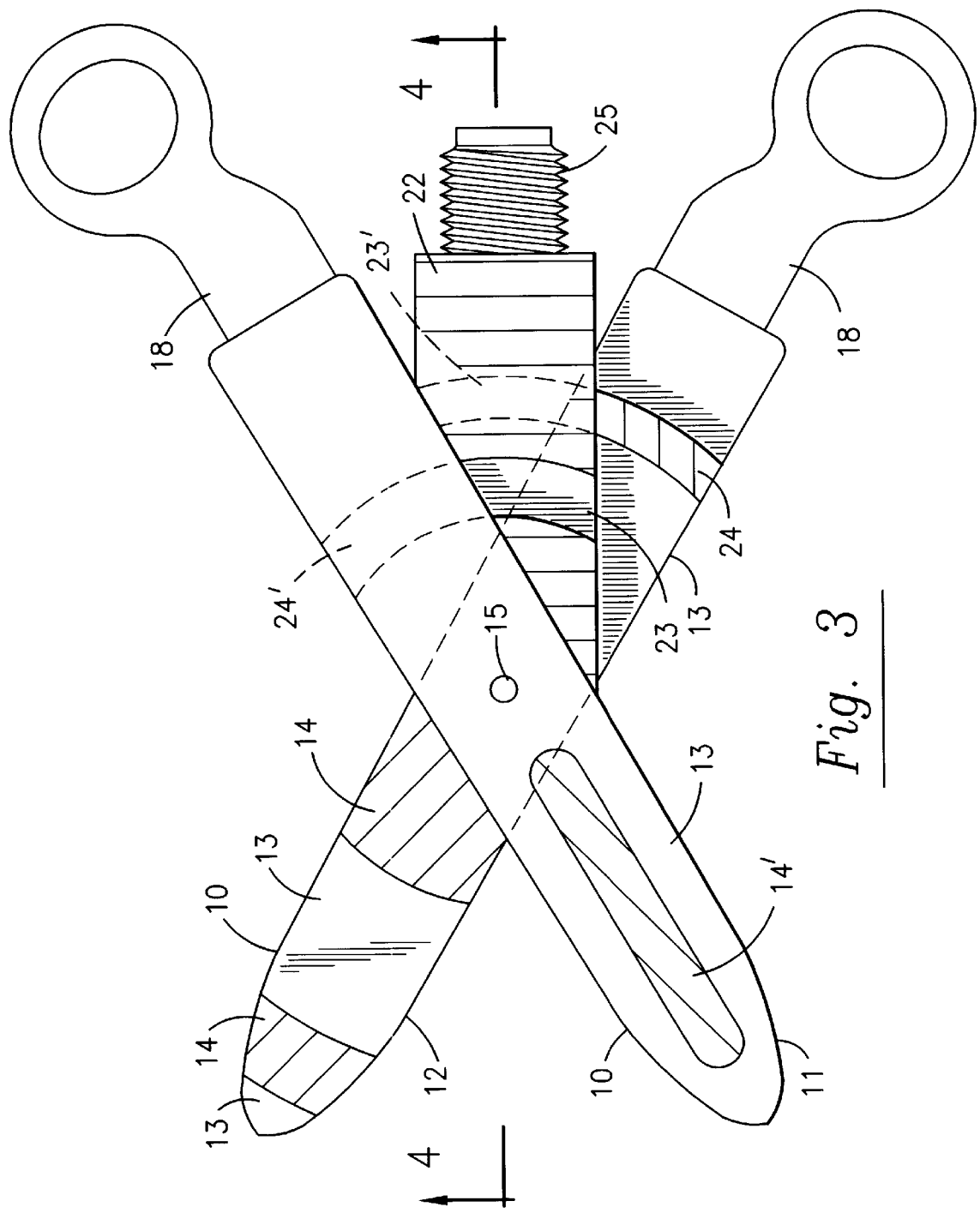
FIG. 3 is a top planar view of a bipolar electrosurgical scissors instrument with the shearing members in the open position and being suitable for use in endoscopic or similar procedures.

Referring now to FIG. 3, there is shown a top plan view of an electrosurgical scissors instrument of the present invention with the shearing members 10 in the open position and which is suitable for endoscopic or similar procedures. From this view, it can be seen that non-conductive portions 14 can be formed as a single integral non-conductive member having surfaces which appear on the interior surface 12 of the shearing members and a supporting portion 14' which extends upwardly from the interior surface 12 through to exterior surface 1 and which mechanically interlocks with conductive portion 13.

Also apparent from FIG. 3 are the curved channels 23 in support 22. Thus, curved channel 23 is shown on the top side of support 22 and curved channel 23', indicated by the dotted line, is located on the far side of support 22. Ridge 24 on interior surface 12 of shearing member 10 rides in curved channel 23' when the shearing members 10 are moved through the full range of scissors-like motion. Ridge 24', indicated by the dotted lines, is located on the far side of shearing member 10 and rides in curved channel 23 through the full range of scissors-like motion. In this manner, additional mechanical support is provided to shearing members 10 in order to minimize mechanical deformation thereof.

Referring now to FIG. 4, there is shown a cross-sectional view along lines 4–4' of FIG. 3 except that the shearing members 11 are in the closed position in FIG. 4 rather than the open position shown in FIG. 3. The cross-sectional view of FIG. 4 shows the lumen 26 which extends through the support 22 and the threaded tube 25 which is adapted for connection to an endoscope or similar apparatus.

Also apparent from FIG. 4 is that two pivot pins 15 may be employed, and these pivot pins extend through conductive portion 13 into support 22 to thereby affix support 22 to shearing members 10. In this embodiment, insulating portion 16 (not shown) is rendered unnecessary since support 22 provides electrical insulation between the shearing members 10.

Further, from FIG. 4 it can be seen that electrically non-conductive portions 14 extend from interior surfaces 12 to exterior surfaces 11 of shearing members 10 in order to provide mechanical support therefor. Thus, each shearing member 10 is typically formed from a single electrical conductive portion 13 and a single electrically non-conductive portion 14 which mechanically interlock with one another to thereby provide strength and solid construction to shearing members 10.

Referring now to FIG. 5, there is shown an alternative embodiment of the present invention which employs external stops 27 for biasing shearing members 10 toward one another so that they remain in close proximity to thereby maximize their cutting efficiency. External stops 27 are affixed via arms 28 to the means for imparting motion 18 in any conventional manner (not shown). External stops 27 may be also spring loaded (not shown) in any conventional manner such as that used for gate cutting tools, for example.

Also depicted in FIG. 5 is an alternative embodiment of support 22 which includes cylindrical projections 29 which fit into recesses 30 in conductive portions 13. Cylindrical projections 29 are adapted to form a bearing surface about which conductive portions 13 can rotate through the full range of scissors-like motion thereof. In this embodiment, the pivot pins 15 (not shown) are preferably flush with the exterior surface 11 of the shearing members 10 and extend into the cylindrical projections 29 of the support 22. In this manner, shearing members 10 are adapted to rotate about cylindrical projections 29 and pivot pins 15 do not interfere with the action of the external stops 27 on the exterior surface 11. In addition, the forward portion of support 22 can function as a load bearing surface against which shearing members 10 ride to thereby provide yet another means of mechanical support to shearing members 10.

Referring now to FIG. 6, FIG. 6 is a cross-section along lines 6–6' of FIG. 5 except that it depicts a different arrangement of the electrically conductive portions 13 and 13'. More particularly, FIG. 6 shows an embodiment of the invention where the electrically conductive portions 13 and 13' run the entire length of interior surfaces 12 of shearing members 10 and 10'. Thus, in this embodiment, electrically conductive portion 13 of first shearing member 10 runs the entire length of the top portion of first shearing member 10 while electrically conductive portion 13' runs the entire length of the bottom portion of second shearing member 10'. It should be noted that electrically conductive portions 13 and 13' do not overlap one another so that there can be no short circuit of the device.

Finally, the present invention also relates to a method of using bipolar electrosurgical instruments to simultaneously cause coagulation in tissue while mechanically severing that tissue. The first step in the method is the provision of first and second shearing members each having an interior surface and an exterior surface and wherein the interior surface of the first shearing member includes an electrically conductive portion and the interior surface of the second shearing member includes an electrically conductive portion. The shearing members are connected together so that the interior surfaces move in opposition through a range of motion in a scissors-like action that defines a cutting point moving along the interior surfaces of the shearing members through the range of motion. The second electrically conductive portion is positioned such that it does not contact the first electrically conductive portion through the full range of scissors-like motion of the shearing members.

The method further includes the steps of connecting the electrodes to a power supply, selecting and maintaining a voltage level output across the power supply, placing the interior surfaces of the shearing members in electrical contact with the tissue to be cut so that the current passes through the tissue between the first and second electrodes and moving the first and second shearing members through the full range of scissors-like motion to simultaneously coagulate and mechanically sever the tissue.

The method can be applied with any of the embodiments of the apparatus which were described above.

The foregoing summary and detailed description are not to be construed as limiting the invention in any way. The scope of the invention is to be determined from the claims appended hereto.

What is claimed is:

1. A bipolar electrosurgical instrument for cutting and coagulating tissue which comprises:
   (a) first and second shearing members each having an interior surface and an exterior surface, the interior surfaces of said shearing members being disposed in opposed relationship and each including a cutting surface comprising an electrically conductive portion and an electrically non-conductive portion, said portions being positioned such that said electrically conductive portions of the opposed interior surfaces of the shearing members do not contact with each other through the full range of a scissors-like motion of at least one of said shearing members;
   (b) means for pivotally joining said first and second shearing members, said means for pivotally joining comprising:
      a pivot pin which extends axially through said first and second shearing members; and
      an electrically non-conductive support having first and second sides and which is located between said first and second shearing members and affixed thereto by said pivot pin, said support comprising at least one curved channel in one of said first and second sides;
   (c) means coupled to at least one of said first and second shearing members for imparting said scissors-like motion to said at least one of said shearing members relative to the other of said shearing members, said means for imparting a scissors-like motion further comprising a ridge adapted to fit into said curved channel and positioned such that said ridge rides in said curved channel through the full range of scissors-like motion of said shearing members; and
   (d) means for applying a voltage across said electrically conductive portions of said interior surfaces of said first and second shearing members.

2. A bipolar electrosurgical instrument as claimed in claim 1 wherein said support is adapted for connection to a distal end of a laparoscope or endoscope.

* * * * *